(12) United States Patent
Aqad et al.

(10) Patent No.: US 8,900,794 B2
(45) Date of Patent: Dec. 2, 2014

(54) PHOTOACID GENERATOR AND PHOTORESIST COMPRISING SAME

(71) Applicant: Rohm and Haas Electronic Materials LLC, Marlborough, MA (US)

(72) Inventors: Emad Aqad, Northborough, MA (US); Cheng-Bai Xu, Southborough, MA (US); Mingqi Li, Shrewsbury, MA (US); Shintaro Yamada, Shrewsbury, MA (US); William Williams, III, Ipswich, MA (US)

(73) Assignee: Rohm and Haas Electronic Materials LLC, Marlborough, MA (US)

( * ) Notice: Subject to any disclaimer, the term of this patent is extended or adjusted under 35 U.S.C. 154(b) by 0 days.

(21) Appl. No.: 13/630,456

(22) Filed: Sep. 28, 2012

(65) Prior Publication Data

US 2013/0084525 A1 Apr. 4, 2013

Related U.S. Application Data

(60) Provisional application No. 61/541,764, filed on Sep. 30, 2011.

(51) Int. Cl.
| | | |
|---|---|---|
| G03F 7/038 | (2006.01) |
| G03F 7/039 | (2006.01) |
| G03F 7/029 | (2006.01) |
| G03F 7/09 | (2006.01) |
| C07C 309/65 | (2006.01) |

(52) U.S. Cl.
USPC ............ 430/270.1; 430/271.1; 430/919; 430/921; 430/922; 430/925; 562/100; 562/113; 562/101; 562/102; 562/103; 562/104; 562/107; 549/31; 549/268; 549/300; 558/51; 558/52; 558/53; 558/54

(58) Field of Classification Search
None
See application file for complete search history.

(56) References Cited

U.S. PATENT DOCUMENTS

| | | |
|---|---|---|
| 6,111,143 A | 8/2000 | Park et al. |
| 6,767,686 B2 | 7/2004 | Uetani et al. |
| 7,301,047 B2 | 11/2007 | Yoshida et al. |
| 7,304,175 B2 | 12/2007 | Harada et al. |
| 7,527,913 B2 | 5/2009 | Yun et al. |
| 7,531,290 B2 | 5/2009 | Kobayashi et al. |
| 7,569,324 B2 | 8/2009 | Kobayashi et al. |
| 7,674,567 B2 | 3/2010 | Yamamoto et al. |
| 8,241,831 B2 | 8/2012 | Jung et al. |
| 8,338,077 B2 | 12/2012 | Li et al. |
| 8,440,384 B2 | 5/2013 | Ebata et al. |
| 2002/0015913 A1 | 2/2002 | Uetani et al. |
| 2004/0234888 A1 | 11/2004 | Lamanna |
| 2006/0210922 A1 | 9/2006 | Nishiyama |
| 2008/0124656 A1 | 5/2008 | Kobayashi et al. |
| 2009/0269700 A1 | 10/2009 | Yonemura et al. |
| 2010/0331440 A1* | 12/2010 | Maruyama et al. ........... 522/108 |
| 2011/0027716 A1 | 2/2011 | Yamaguchi et al. |
| 2011/0171576 A1 | 7/2011 | Yamaguchi et al. |

* cited by examiner

Primary Examiner — Sin J. Lee
(74) Attorney, Agent, or Firm — Cantor Colburn LLP

(57) ABSTRACT

A photoacid generator compound has the formula (I):

$$[A\text{-}(CHR^1)_p]_k\text{-}(L)\text{-}(CH_2)_m\text{-}(C(R^2)_2)_n\text{-}SO_3^-Z^+ \quad (I)$$

wherein A is a substituted or unsubstituted, monocyclic, polycyclic, or fused polycyclic $C_5$ or greater cycloaliphatic group optionally comprising O, S, N, F, or a combination comprising at least one of the foregoing, $R^1$ is H, a single bond, or a substituted or unsubstituted $C_{1-30}$ alkyl group, wherein when $R^1$ is a single bond, $R^1$ is covalently bonded to a carbon atom of A, each $R^2$ is independently H, F, or $C_{1-4}$ fluoroalkyl, wherein at least one $R^2$ is not hydrogen, L is a linking group comprising a sulfonate group, a sulfonamide group, or a $C_{1-30}$ sulfonate or sulfonamide-containing group, Z is an organic or inorganic cation, p is an integer of 0 to 10, k is 1 or 2, m is an integer of 0 or greater, and n is an integer of 1 or greater. A precursor compound to the photoacid generator, a photoresist composition including the photoacid generator, and a substrate coated with the photoresist composition, are also disclosed.

22 Claims, No Drawings

PHOTOACID GENERATOR AND PHOTORESIST COMPRISING SAME

CROSS REFERENCE TO RELATED APPLICATION

This application claims priority to provisional U.S. Application No. 61/541,764, filed on Sep. 30, 2011, the content of which is incorporated herein by reference in its entirety.

BACKGROUND

Advanced lithographic techniques such as 193 nm immersion lithography have been developed to achieve high quality and smaller feature sizes in microlithography processes, for purposes of forming ever-smaller logic and memory transistors. It is important to achieve both smaller critical dimension (CD) in the imaged photoresist used in the microlithography process, and for the photoresists to provide both the lowest line edge roughness (LER) and line width roughness (LWR), while still retaining good process control tolerances such as high exposure latitude (EL) and a wide depth of focus (DOF).

To meet the challenges for resist materials raised by high resolution lithography, tailor-made photoacid generators (PAGs) with controlled acid diffusion and improved miscibility with polymers are very important. It has been found that the structure of the PAG anion plays a critical role in the overall performance of a photoresist by affecting the interaction of the photoacid generator with other photoresist components. These interactions, affect the diffusion characteristics of the photogenerated acid. PAG structure and size can therefore affect the homogenous distribution of the PAG in the photoresist film. Imaged photoresists can exhibit defects such as T-topping, foot formation and notching/undercut where the PAG is not uniformly distributed within the photoresist film.

While a variety of photoacid generators (PAGs) used for formulating photoresists are found in prior art, such as those disclosed in U.S. Pat. No. 7,304,175, a need remains for photoresist compositions including PAGs having greater diffusion control and attendant properties such as resist profile.

STATEMENT OF INVENTION

One or more of the above and other deficiencies of the prior art may be overcome by a photoacid generator in accordance with the invention, having the formula (I):

$$[A\text{-}(CHR^1)_p]_k\text{-}(L)\text{-}(CH_2)_m\text{---}(C(R^2)_2)_n\text{---}SO_3^-Z^+ \quad (I)$$

wherein A is a substituted or unsubstituted, monocyclic, polycyclic, or fused polycyclic $C_5$ or greater cycloaliphatic group, $R^1$ is H, a single bond, or a substituted or unsubstituted $C_{1-30}$ alkyl group, wherein when $R^1$ is a single bond, $R^1$ is covalently bonded to a carbon atom of A, each $R^2$ is independently H, F, or $C_{1-4}$ fluoroalkyl, wherein at least one $R^2$ is not hydrogen, L is a linking group comprising a sulfonate group, a sulfonamide group, or a $C_{1-30}$ sulfonate or sulfonamide-containing group, Z is an organic or inorganic cation, and p is an integer of 0 to 10, k is 1 or 2, m is an integer of 0 or greater, and n is an integer of 1 or greater.

Also disclosed is a compound having the formula:

$$M^+\text{-O---}SO_2\text{---}(C(R^2)_2)_n\text{---}(CH_2)_m\text{---}X$$

wherein each $R^2$ is independently H, F, a $C_{1-4}$ fluoroalkyl, wherein at least one $R^2$ is not hydrogen, X is a functional group including a halogen, sulfonate, or carboxylate, $M^+$ is an organic or inorganic cation, and m is an integer of 0 or greater, and n is an integer of 1 or greater.

A photoresist composition comprises an acid-sensitive polymer, and the above photoacid generator compound of formula (I).

A coated substrate further comprises (a) a substrate having one or more layers to be patterned on a surface thereof; and (b) a layer of the photoresist composition which includes the photoacid generator compound, over the one or more layers to be patterned.

DETAILED DESCRIPTION

Disclosed herein is a novel class of photoacid generator compounds having a sulfonate or sulfonamide linking group connecting a sterically bulky group with a sulfonate salt. The photoacid generators include sterically bulky groups including cycloaliphatic structures such as caged alkyl groups. Exemplary such groups include adamantane structures, norbornane structures, fused polycyclic lactones, and other such structures. The cycloaliphatic groups are linked to a fluorinated sulfonate group by a linking group that includes a sulfonate or sulfonamide group.

The photoacid generators provide improved control of acid diffusion and miscibility with photoresist polymers in photoresist compositions. Improvements in properties such as mask error factor (MEF), and exposure latitude (EL) are obtained by using the sulfonate and sulfonamide-linked PAGs.

The photoacid generators disclosed herein include those having the formula (I):

$$[A\text{-}(CHR^1)_p]_k\text{-}(L)\text{-}(CH_2)_m\text{---}(C(R^2)_2)_n\text{---}SO_3^-Z^+ \quad (I)$$

wherein A is a substituted or unsubstituted, monocyclic, polycyclic, or fused polycyclic $C_5$ or greater cycloaliphatic group. As used herein, "substituted" means including a substituent such as a halogen (i.e., F, Cl, Br, I), hydroxy, amino, thiol, carboxyl, carboxylate, amide, nitrile, thiol, sulfide, disulfide, nitro, a $C_{1-10}$ alkyl, a $C_{1-10}$ alkoxy, a $C_{6-10}$ aryl, a $C_{6-10}$ aryloxy, a $C_{7-10}$ alkyl aryl, a $C_{7-10}$ alkyl aryloxy, or a combination comprising at least one of the foregoing. It will be understood that any group or structure disclosed with respect to the formulas herein may be so substituted unless otherwise specified, or where such substitution would significantly adversely affect the desired properties of the resulting structure. Also as used herein, the prefix "halo-" means that the group includes any halogen or combination thereof (F, Cl, Br, I). A preferred halogen is fluorine. Optionally, A further includes a heteroatom including O, S, N, F, or a combination comprising at least one of the foregoing. For example, where A includes oxygen, the structure of A can include an ether or lactone moiety, or where A includes sulfur, the structure of A can include a sultone or sulfonate or sulfam moiety.

Preferably, A is a fused ring $C_{5-50}$ polycycloaliphatic group, having either all carbon in a ring structure, or an internal lactone or sulfonate (sultone) moiety. Preferably, A is a fused ring $C_{8-35}$ polycycloaliphatic group. Examples of such groups include adamantane structures such as 1-or 2-substituted adamantyl, and 1-or 2-substituted hydroxyadamantyl, norbornene endo lactones or sultones, and other $C_{6-10}$ polycyclic lactone or sultone-containing groups.

Also in formula (I), $R^1$ is H, a single bond, or a substituted or unsubstituted $C_{1-30}$ alkyl group, wherein when $R^1$ is a single bond, $R^1$ is covalently bonded to a carbon atom of A. Each $R^2$ is independently H, F, or $C_{1-4}$ fluoroalkyl, wherein at least one $R^2$ is not hydrogen.

Further in formula (I), L is a linking group comprising a sulfonate group of the formula —O—S(O)$_2$—, a sulfonamide group, or a $C_{1-30}$ sulfonate or sulfonamide-containing group.

The sulfonamide group is preferably of the formula —N(R³)—S(O)₂—, wherein R³ is H, alkyl, aryl, or aralkyl. Thus, L can be, for example, a sulfonate or sulfonamide group alone, or a $C_{1-30}$ sulfonate or sulfonamide-containing linking group. L can further optionally comprise a heteroatom comprising O, S, N, F, or a combination comprising at least one of the foregoing heteroatoms.

Z is an organic or inorganic cation. As used herein, "organic cation" includes any cation substituted with carbon at the cationic center including an ammonium salt, a phosphonium salt, an iodonium salt, a sulfonium salt, a carbonium salt, an oxonium salt, an organotransition metal salt (e.g., salts of carbon-substituted iron, nickel, cobalt, manganese, titanium, copper, molybdenum, zinc, etc.), or an organo main-group metal salt (e.g., salts of carbon substituted aluminum, tin, gallium, antimony, etc.). Preferred organic cations include onium cations. Preferred onium cations include iodonium or sulfonium cations. Also as used herein, "inorganic cation" means any cation not based on carbon, such as alkali metal cations (Li, Na, K, Rb, Cs), alkaline earth metal cations (Ca, Ba, Sr), transition metal cations and complexes, and non-organic cations of nitrogen, phosphorus, and sulfur.

Further in formula (I), p is an integer of 0 to 10, k is 1 or 2, m is an integer of 0 or greater, and n are each independently an integer of 1 or greater. Preferably, m and n are independently integers of from 1 to 10.

Preferably, the photoacid generator includes compounds having the formulas (IIa) or (IIb):

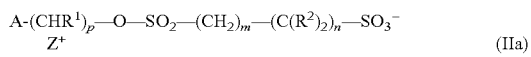
(IIa)

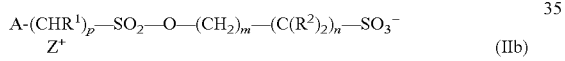
(IIb)

wherein A, R¹, R² p, m, n, and Z are as defined for formula (I).

Preferably, in formulas (IIa) and (IIb), R¹ is H, or a substituted or unsubstituted $C_{1-20}$ alkyl group. Each R² is independently H or F, wherein at least the two R² groups nearest the sulfonate are fluorine, p is 0 or 1, m and n are independently integers of from 1 to 4, and Z is an iodonium or sulfonium cation.

Also preferably, the photoacid generator compound includes compounds having the formulas (IIIa) or (IIIb):

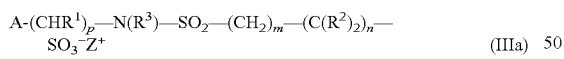
(IIIa)

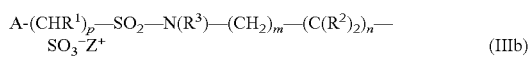
(IIIb)

wherein A, R¹, R² p, m, n, and Z are as defined for formula (I), and R³ is H, a $C_{1-20}$ alkyl group, or A-(CHR¹)$_p$—. Where R³ is A-(CHR¹)$_p$—, it will be appreciate that this group may be the same as or different from the other group A-(CHR¹)$_p$—.

Preferably, in formula (IIIa) and (IIIb), R¹ is H, a substituted or unsubstituted $C_{1-5}$ alkyl group, or a A-(CHR¹)$_p$— group. Each R² is independently H or F, wherein at least the two R² groups nearest the sulfonate are fluorine, R³ is H or a $C_{1-4}$ alkyl, p is 0 or 1, m and n are independently integers of from 1 to 4, and Z is an iodonium or sulfonium cation.

Exemplary compounds of formulas (I), (IIa), (IIb), (IIIa) and (IIIb) include those having the formulas (IV) to (XII):

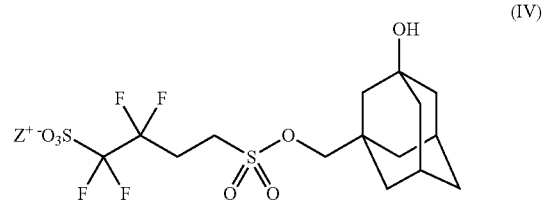
(IV)

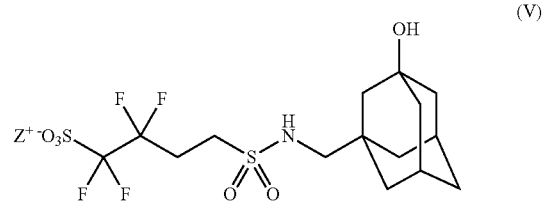
(V)

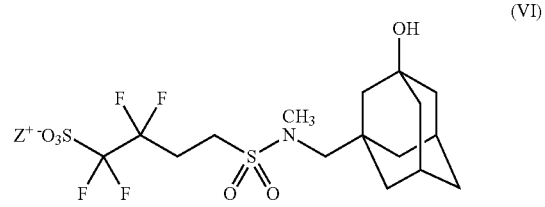
(VI)

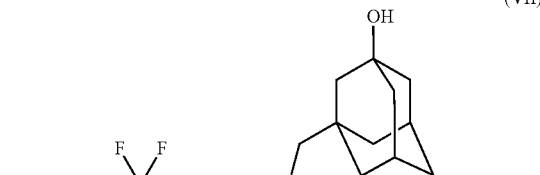
(VII)

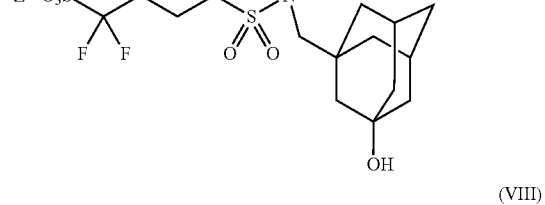
(VIII)

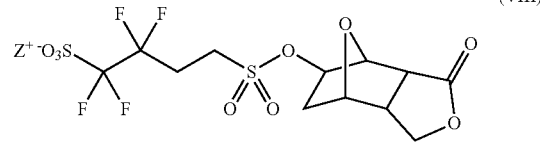
(IX)

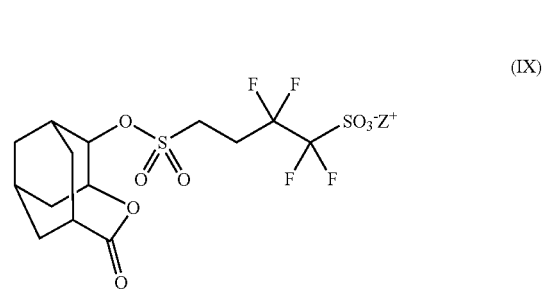
(X)

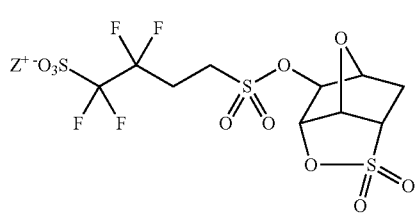
(XI)

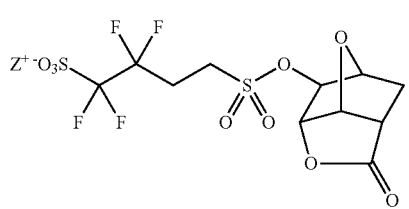
(XII)

wherein Z is as defined in formula (I).

Preferably, Z is an organic cation based on an organosulfonium structure. Preferred such organic cations include those in which Z is a cation of the formula (XIII):

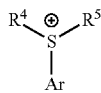
(XIII)

wherein $R^4$ and $R^5$ are independently substituted or unsubstituted $C_{1-20}$ alkyl, $C_{1-20}$ fluoroalkyl, $C_{3-20}$ cycloalkyl, $C_{3-20}$ fluorocycloalkyl, $C_{2-20}$ alkenyl, $C_{2-20}$ fluoroalkenyl, $C_{6-20}$ aryl, $C_{6-20}$ fluoroaryl, $C_{5-20}$ heteroaryl, $C_{7-20}$ aralkyl, $C_{7-20}$ fluoroaralkyl, $C_{6-20}$ heteroaralkyl, where $R^4$ and $R^5$ are separate or connected by a single bond, and Ar is a $C_{5-30}$ aromatic-containing group.

More preferred organic cations include those having at least one substituted aromatic ring attached to the sulfonium center. Such cations include those of the formulas (XIV), (XV), or (XVI):

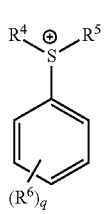
(XIV)

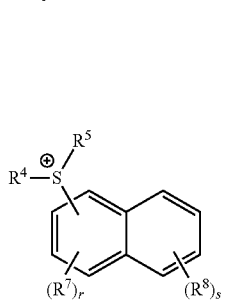
(XV)

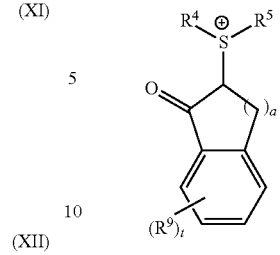
(XVI)

wherein $R^4$ and $R^5$ are independently substituted or unsubstituted $C_{1-20}$ alkyl, $C_{1-20}$ fluoroalkyl, $C_{3-20}$ cycloalkyl, $C_{3-20}$ fluorocycloalkyl, $C_{2-20}$ alkenyl, $C_{2-20}$ fluoroalkenyl, $C_{6-20}$ aryl, $C_{6-20}$ fluoroaryl, $C_{5-20}$ heteroaryl, $C_{7-20}$ aralkyl, $C_{7-20}$ fluoroaralkyl, or $C_{6-20}$ heteroaralkyl, where $R^4$ and $R^5$ are separate or connected by a single bond; $R^6$, $R^7$, $R^8$ and $R^9$ are each independently H, a halogen, $C_{1-20}$ alkyl, $C_{1-20}$ fluoroalkyl, $C_{1-20}$ alkoxy, $C_{1-20}$ fluoroalkoxy, $C_{1-20}$ thioalkoxy, $C_{1-20}$ fluorothioalkoxy, $C_{1-20}$ alkoxycarbonyl, $C_{1-20}$ fluoroalkoxycarbonyl, $C_{1-20}$ thioalkoxycarbonyl, $C_{1-20}$ fluorothioalkoxycarbonyl, $C_{3-20}$ cycloalkyl, $C_{3-20}$ fluorocycloalkyl, $C_{3-20}$ cycloalkoxy, $C_{3-20}$ fluorocycloalkoxy, $C_{2-20}$ alkenyl, $C_{2-20}$ fluoroalkenyl, $C_{6-20}$ aryl, $C_{6-20}$ fluoroaryl, $C_{6-20}$ aryloxy, $C_{6-20}$ fluoroaryloxy, $C_{5-20}$ heteroaryl, $C_{5-20}$ heteroaryloxy, $C_{7-20}$ aralkyl, $C_{7-20}$ fluoroaralkyl, $C_{7-20}$ aralkyloxy $C_{7-20}$ fluoroaralkyloxy, or $C_{6-20}$ heteroaralkyl, or $C_{6-20}$ heteroaralkyloxy, wherein $R^6$, $R^7$, $R^8$ and $R^9$ are each independently unsubstituted or further substituted to include an acid-labile group, a base-labile group, or a base-soluble group, and q is an integer of 1 to 5, r is an integer of 0 to 3, s is an integer of 0 to 4, t is an integer of 0 to 4, and a is an integer of 0 to 4.

Most preferred cations Z include those of the formula (XVII), (XVIII), (XIX), or (XX):

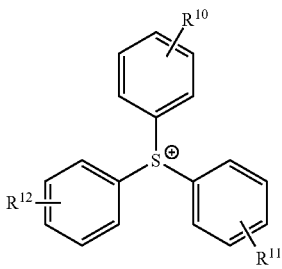
(XVII)

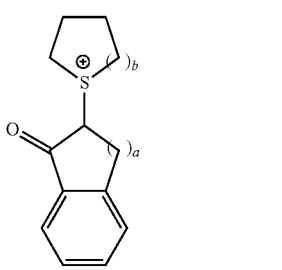
(XVIII)

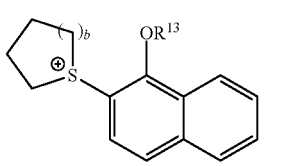
(XIX)

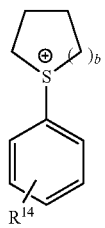

(XX)

wherein $R^{10}$, $R^{11}$, $R^{12}$ and $R^{14}$ are independently H, a halogen, $C_{1-10}$ alkyl, $C_{1-10}$ fluoroalkyl, $C_{1-10}$ alkoxy, $C_{1-10}$ fluoroalkoxy, $C_{3-10}$ cycloalkyl, $C_{3-10}$ fluorocycloalkyl, $C_{3-10}$ cycloalkoxy, or $C_{3-10}$ fluorocycloalkoxy, $R^{13}$ is H, $C_{1-10}$ alkyl, $C_{1-10}$ fluoroalkyl, $C_{3-10}$ cycloalkyl, or $C_{3-10}$ fluorocycloalkyl, and a and b are each independently 1 or 2.

The above photoresist compounds derive from compounds having the formula (XXI):

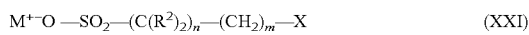

(XXI)

wherein each $R^2$ is independently H, F, a $C_{1-4}$ fluoroalkyl, where at least one $R^2$ is not hydrogen, X is a functional group including a halogen, sulfonate, sulfonamide, or carboxylate, $M^+$ is an organic or inorganic cation, and m is an integer of 0 or greater, and n is an integer of 1 or greater. It will thus be appreciated that the formula of (XXI) includes the substructures of the linking group L in formula (I), and the substructure of the halogenated portion of the superacid salt.

The photoresist compounds can be prepared by the derivatization of a compound of the formula (XXI) by, for example, forming the sulfonic acid halide of the salt by treatment with a halogenating compound such a thionyl or sulfonyl chloride, reaction with the amine or alcohol of an caged polycyclic aliphatic compound such as a substituted or unsubstituted adamantyl methyl compound, norbornane compound, etc.; forming the sulfonic acid from the functional group (where for example, X is Cl, Br, or I in formula (XXI)) from sodium dithionite ($Na_2S_2O_4$) and oxidation with a peroxide such as hydrogen peroxide; then cation exchange with an onium salt to form the photoacid generator.

A photoresist composition is also disclosed, which includes the molecular glass compound, a solvent, and a photoacid generator. Optionally the photoresist includes a second acid sensitive polymer, and an amine or amide additive.

The second acid-sensitive polymer may be any polymer suitable for formulating photoresists for use at 193 nm Such acid-sensitive polymers include an acid sensitive polymer comprising acid sensitive groups and lactone-containing groups, where the acid sensitive group deprotects a base-soluble group on exposure to acid.

The photoresist composition may further include an amine or amide compound, referred to herein as a quencher. Quenchers may more broadly include, for example, those based on hydroxides, carboxylates, amines, imines, and amides. In an embodiment, a useful quencher is an amine, an amide, or a combination comprising at least one of the foregoing. Preferably, such quenchers include C1-30 organic amines, imines, or amides, or may be a $C_{1-30}$ quaternary ammonium salt of a strong base (e.g., a hydroxide or alkoxide) or a weak base (e.g., a carboxylate). Examples of quenchers include amines such as Troger's base, a hindered amine such as diazabicycloundecene (DBU) or diazabicyclononene (DBN), N-protected amines such as N-t-butylcarbonyl-1,1-bis(hydroxymethyl)-2-hydroxyethylamine (TB OC-TRIS), or ionic quenchers including quaternary alkyl ammonium salts such as tetrabutylammonium hydroxide (TBAH) or tetrabutyl ammonium lactate.

Other components of the photoresist may include solvents and surfactants.

Solvents generally suitable for dissolving, dispensing, and coating the components include anisole, alcohols including ethyl lactate, 1-methoxy-2-propanol, and 1-ethoxy-2 propanol, esters including n-butylacetate, 1-methoxy-2-propyl acetate, methoxyethoxypropionate, ethoxyethoxypropionate, ketones including cyclohexanone and 2-heptanone, and a combination comprising at least one of the foregoing solvents.

Surfactants include fluorinated and non-fluorinated surfactants, and are preferably non-ionic. Exemplary fluorinated non-ionic surfactants include perfluoro $C_4$ surfactants such as FC-4430 and FC-4432 surfactants, available from 3M Corporation; and fluorodiols such as POLYFOX PF-636, PF-6320, PF-656, and PF-6520 fluorosurfactants from Omnova.

The photoresist composition disclosed herein includes the photoacid generator in the photoresist composition in an amount of 0.01 to 30 wt %, preferably 0.1 to 20 wt %, and more preferably 0.5 to 15 wt %, based on the total weight of solids. The polymer may be included in an amount of 50 to 99 wt %, preferably 55 to 95 wt %, more preferably 60 to 90 wt %, and more preferably 65 to 90 based on the total weight of solids. It will be understood that "polymer" used in this context of a component in a photoresist may mean the acid sensitive polymer or copolymer, or a combination of polymers or copolymers and any other polymer useful in a photoresist. A surfactant may be included in an amount of 0.01 to 5 wt %, preferably 0.1 to 4 wt %, and more preferably 0.2 to 3 wt %, based on the total weight of solids. A quencher may be included in relatively small amounts of for example, from 0.03 to 5 wt % based on the total weight of solids. Other additives may be included in amounts of less than or equal to 30 wt %, preferably less than or equal to 20%, or more preferably less than or equal to 10%, based on the total weight of solids. The total solids content for the photoresist composition may be 0.5 to 50 wt %, preferably 1 to 45 wt %, more preferably 2 to 40 wt %, and more preferably 5 to 35 wt %, based on the total weight of solids and solvent. It is understood that the solids include polymer, photoacid generator, quencher, surfactant, and any optional additives, exclusive of solvent.

The photoresist composition disclosed herein may be used to form a film comprising the photoresist, where the film on the substrate constitutes a coated substrate. Such a coated substrate includes: (a) a substrate having one or more layers to be patterned on a surface thereof; and (b) a layer of the photoresist composition over the one or more layers to be patterned. Preferably, patterning is carried out using ultraviolet radiation at wavelength of less than 248 nm, and in particular, at 193 nm. Preferably, a patternable film comprises the photoacid generator.

Substrates may be any dimension and shape, and are preferably those useful for photolithography, such as silicon, silicon dioxide, silicon-on-insulator (SOI), strained silicon, gallium arsenide, coated substrates including those coated with silicon nitride, silicon oxynitride, titanium nitride, tantalum nitride, ultrathin gate oxides such as hafnium oxide, metal or metal coated substrates including those coated with titanium, tantalum, copper, aluminum, tungsten, alloys thereof, and combinations thereof. Preferably, the surfaces of substrates herein include critical dimension layers to be patterned including, for example, one or more gate-level layers or other critical dimension layer on the substrates for semiconductor manufacture. Such substrates may preferably include silicon, SOI, strained silicon, and other such substrate materials, formed as circular wafers having dimensions such as, for example, 200 mm, 300 mm, or larger in diameter, or other dimensions useful for wafer fabrication production.

Further, a method of forming an electronic device includes (a) applying a layer of a photoresist composition including the photoacid generator compound on a surface of the substrate; (b) patternwise exposing the photoresist composition layer to activating radiation; and (c) developing the exposed photoresist composition layer to provide a resist relief image.

Applying may be accomplished by any suitable method, including spin coating, spray coating, dip coating, doctor blading, or the like. Applying the layer of photoresist is preferably accomplished by spin-coating the photoresist in solvent using a coating track, in which the photoresist is dispensed on a spinning wafer. During dispense, the wafer may be spun at a speed of up to 4,000 rpm, preferably from about 500 to 3,000 rpm, and more preferably 1,000 to 2,500 rpm. The coated wafer is spun to remove solvent, and baked on a hot plate to remove residual solvent and free volume from the film to make it uniformly dense.

Patternwise exposure is then carried out using an exposure tool such as a stepper, in which the film is irradiated through a pattern mask and thereby is exposed patternwise. The method preferably uses advanced exposure tools generating activating radiation at wavelengths capable of high resolution including 193 nm immersion lithography, in which exposure using the activating radiation decomposes the PAG in the exposed areas, generating acid and decomposition by-products. The acid then effects a chemical change in the polymer (e.g., deblocking the acid sensitive group to generate a base-soluble group, or alternatively, catalyzing a cross-linking reaction in the exposed areas).

The invention is further illustrated by the following examples. All compounds and reagents used herein are available commercially except where a procedure is provided below.

Triphenylsulfonium 1,1,2,2-tetrafluoro-4-(((-3-hydroxyadamantan-1-yl)methoxy)sulfonyl)butane-1-sulfonate (TPS AdOH-STFBS) was synthesized in five steps as described below.

In the first step, the synthesis of PAG Intermediate Compound 1 (Sodium 4-bromo-3,3,4,4-tetrafluorobutane-1-sulfonate) was carried out as follows. A 250 mL round bottom flask was charged with 1,4-dibromo-1,1,2,2-tetrafluorobutane (50.00 g, 174 mmol), 87 mL deionized water, 87 mL n-butanol, and 24.12 g (191 mmol) sodium sulfite, and the mixture was heated to reflux and stirred under nitrogen for 6 days, at which time heat was removed and the reaction cooled to less than reflux temperature while standing to separate the phases. The aqueous phase was separated from the organic (n-butanol containing) phase, extracted with additional n-butanol (2×50 mL), and the organic phases were combined and reduced to 50 mL total volume by rotary evaporation under reduced pressure. The resulting white slurry was stirred rapidly and 400 mL methyl t-butyl ether (MTBE) was added. The slurry was then stirred an additional 15 min and the solids collected by vacuum filtration. The resulting white solid was washed with MTBE, and dried in vacuo at ambient temperature overnight, to yield 62.73 g of the intermediate as a white solid, which was used in the next step without further purification.

In the second step, the synthesis of PAG Intermediate Compound 2 (4-Bromo-3,3,4,4-tetrafluorobutane-1-sulfonyl chloride) was carried out as follows. A 500 mL round bottom flask was charged with 28.61 g of crude sodium 4-bromo-3,3,4,4-tetrafluorobutane-1-sulfonate (PAG Intermediate Compound 1) and 92 mL thionyl chloride. The thick suspension was stirred at ambient temperature under nitrogen until gas evolution ceased, then 450 µL N,N-dimethylformamide (DMF) was added. Stirring was continued at ambient temperature until gas evolution ceased, then the reaction was heated to reflux with stirring under nitrogen for 16 hours. Unreacted thionyl chloride was removed by rotary evaporation, the residue was dissolved in 400 mL dichloromethane, and the resulting dichloromethane solution was washed with deionized water (400 mL), and dried over $MgSO_4$. The dichloromethane solvent was removed by rotary evaporation at 30° C., and the residual oil dried in vacuo at ambient temperature for 3 hours, to yield 21.35 g of PAG intermediate compound 2 as a clear yellow oil.

In the third step, the synthesis of PAG Intermediate Compound 3 (3-hydroxyadamantan-1-ylmethyl 4-bromo-3,3,4,4-tetrafluorobutane-1-sulfonate; AdOH STFBBr) was carried out as follows. To a 1 L round bottom flask was added 12.02 g (65.9 mmol) of 3-(hydroxymethyl)adamantan-1-ol in 280 mL acetonitrile and 5.61 mL (69 4 mmol) pyridine by stirring and warming The reaction was cooled and 4-bromo-3,3,4,4-tetrafluorobutane-1-sulfonyl chloride (PAG Intermediate Compound 2; 21.35 g, 69.4 mmol) was added dropwise to the rapidly stirred warm solution, followed by quantitative transfer of any residues by rinsing the flask with acetonitrile (2×10 mL). The reaction was stirred at ambient temperature under nitrogen for 16 hours, at which time the solvent was removed under reduced pressure and the residual oil stirred with 500 mL of isopropyl acetate. The resulting white precipitate was removed by vacuum filtration, and the filter cake washed with minimal isopropyl acetate. The isopropyl acetate filtrates were combined and washed with 1 N HCl and saturated aqueous $NaHCO_3$ (200 mL each), dried over $MgSO_4$, and the solvent removed under reduced pressure to give 29.55 g of PAG Intermediate Compound 3 as a white solid which was used without further purification.

In the fourth step, the synthesis of PAG Intermediate Compound 4 (1,1,2,2-tetrafluoro-4-((3-hydroxyadamantan-1-yl)methoxy)sulfonyl)butane-1-sulfonate) was carried out as follows. In a 1 L round bottom flask was dissolved intermediate compound 1-3 (29.55 g, 65.2 mmol) in 140 mL acetonitrile. Sodium dithionite (17.03 g, 97.8 mmol) and sodium bicarbonate (8.22 g, 97.8 mmol) were combined and dissolved in 150 mL deionized water. The aqueous solution was then added to the stirred acetonitrile solution and the reaction stirred at ambient temperature under nitrogen for 16 hours. Additional charges of each of sodium dithionite (17.03 g, 97.8 mmol) and sodium bicarbonate (8.22 g, 97.8 mmol) were combined and dissolved in another 150 mL deionized water and added to the reaction, and the reaction stirred for an additional 20 hours. Reaction monitoring by $^{19}F$ NMR indicated 75% completion (molar basis). The reaction was stirred under nitrogen at 70° C. 16 hours. Reaction completion was confirmed by $^{19}F$ NMR. Acetonitrile (160 mL) was then added to the reaction, the aqueous phase was saturated with NaCl, and the reaction was stirred rapidly for 30 minutes to homogenize it. The phases were separated and the aqueous phase extracted with acetonitrile (2×300 mL). The acetonitrile phases were combined and the solvent removed to give 32.39 g crude sulfinate intermediate, which was dissolved in 100 mL deionized water and 200 mL acetonitrile. To the stirred solution was added $Na_2WO_4 \cdot 2H_2O$ (21 mg, 65 µmol) followed by $H_2O_2$ (30 w/w % aqueous, 14.82 g, 130.4 mmol). The reaction was stirred at ambient temperature for 64 hours.

The reaction was then cooled using an ice bath, and sodium bisulfite (10.18 g, 97.8 mmol) was added with stirring. After 10 minutes the ice bath was removed, the reaction was saturated with NaCl, and stirred rapidly for 1 hour to homogenize it. The phases were then separated and the aqueous phase extracted with 250 mL acetonitrile. The solvent of the combined organic phases was removed by rotary evaporation, the resulting residue redissolved in 250 mL acetonitrile and filtered by vacuum filtration and washed with 100 mL acetonitrile. The filtrate was evaporated on the rotary evaporator at 40° C. to give a clear gum, which was dissolved in 50 mL acetonitrile and poured slowly into 3 L of rapidly stirred methyl t-butyl ether (MTBE). The supernatant was decanted and the solids dried under vacuum to yield 17.0 g of the PAG Intermediate Compound 4 as a white solid.

In the fifth step, the synthesis of the PAG compound triphenylsulfonium 1,1,2,2-tetrafluoro-4-4(-3-hydroxyadamantan-1-yl)methoxy)sulfonyl)butane-1-sulfonate (TPS AdOH-STFBS) was carried out as follows. To a stirred mixture of 200 mL dichloromethane and 200 mL deionized water was added Na AdOH STFBS (intermediate compound 1-4; 17.0 g, 35.7 mmol) and triphenylsulfonium bromide (11.64 g, 33.9 mmol). The biphasic mixture was stirred under nitrogen at ambient temperature for 10 hours, at which time the phases were separated. The organic phase was washed with 18 mΩ deionized water (2×200 ml). Additional dichloromethane (200 mL) was added to the organic phase to promote separation, and the organic phase was then washed with additional deionized water (4×200 mL). The organic phase was then filtered through heavy pleated filter paper, and the solvent removed by rotary evaporation at 30° C. The resulting residue was dissolved in 50 mL dichloromethane and poured slowly into 2 L of rapidly stirred methyl t-butyl ether. The suspension was then stirred 1 hour, during which time it congealed and was allowed to stand 30 minutes. The solids were then vacuum filtered, washed with MTBE, and dried in vacuo to yield 18.05 g (68%) of TPS AdOH-STFBS as a white solid.

The TPS AdOH-STFBS photoacid generator compound of the above example was then evaluated lithographically.

The photoresists were formulated using the components and proportions shown in Table 1, below.

A photoresist polymer (A1) for use in the lithographic evaluations (below) is prepared using monomers M1-M5 below, according to the following procedure.

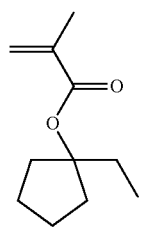

M1

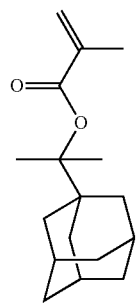

M2

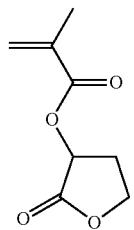

M3

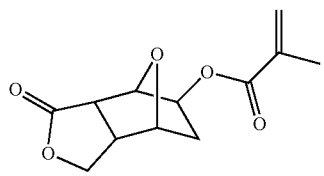

M4

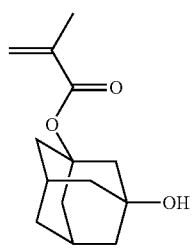

M5

A solution of 1-ethylcyclopentyl methacrylate (ECPMA, M1; 20 mmol), 1-isopropyl-adamantanyl methacrylate (IAM, M2; 20 mmol), 2-oxo-tetrahydro-furan-3-yl methacrylate (α-GBLMA, M3; 30 mmol), 3-oxo-4,10-dioxa-tricyclo[5.2.1.02,6]dec-8(or 9)-yl methacrylate (ODOTMA, M4; 20 mmol), and 3-hydroxy-adamantanyl methacrylate (HAMA, M5; 10 mmol) dissolved in 30 g of tetrahydrofuran (THF) is degassed by bubbling with nitrogen and charged to a 500 ml flask equipped with a condenser, nitrogen inlet and mechanical stirrer along with an additional 10 g of degassed THF. The solution is brought to reflux, and 6 g of dimethyl-2,2-azodiisobutyrate is dissolved in 5 g of THF and charged in to the flask. The polymerization mixture is then stirred for about 4 hours at reflux, after which time the reaction is diluted with 5 g of THF and the polymerization mixture cooled to room temperature. The polymer is precipitated by addition to 1.0 L of isopropanol, collected by filtration, re-precipitated by dissolving in 50 g THF and addition to another 1.0 L isopropanol, and collected and dried under vacuum at 45° C. for 48 h. to yield photoresist polymer poly(IAM/ECPMA/α-GBLMA/ODOTMA/HAMA). Mw=8,000.

The photoresist was formulated using the components and proportions shown in Table 1 to provide a photoresist and a comparative photoresist. Note that for each, the PAG (see table), base (t-butyloxycarbonyl-4-hydroxypyridine, TBOC-4HP), and surface leveling agent (SLA; also referred to as surfactant; PF 656, available from Omnova), are shown as a weight percentage based on the total solids content of the photoresist, with the balance of the solids being the polymer. The photoresists are further formulated using as solvents propylene glycol methyl ether acetate (S1) and methyl 2-hydroxyisobutyrate (S2) in a 1:1 ratio by weight. The photoresist and comparative photoresist were each diluted to a final solids of 4 wt %. Photoresist formulation compositions for the comparative example 1 (comparative photoresist) and example 1 (photoresist prepared using TPS AdOH-STFBS), are shown in Table 1 below:

TABLE 1

| Example | Polymer (wt %) | PAG | PAG (wt %) | Base (wt %) | SLA ((wt %) |
|---|---|---|---|---|---|
| CEx. 1 | 89.29 | Triphenylsulfonium perfluorobutane sulfonate | 9.58 | 1.03 | 0.1 |
| Ex. 1 | 86.66 | TPS AdOH-STFBS | 12.21 | 1.03 | 0.1 |

Photoresists from Example 1 and Comparative Example 1 were lithographically processed as follows.

The photoresist was spin coated onto a 200 mm silicon wafer having an organic antireflective coating (AR™77, Rohm and Haas Electronic Materials LLC, baked at) and baked at 110° C. for 60 seconds, to form a resist film 100 nm in thickness. The photoresist was exposed with ArF excimer laser radiation (193 nm) using an ASML/1100 exposure tool (manufactured by ASML) with a numerical aperture (NA) of 0.75, under annular illumination with outer/inner sigma of 0.89/0.64 and focus offset/step 0.10/0.05. A line-space pattern mask targeting a linewidth of 90 nm and a pitch of 180 nm was used to image the features.

The patterned resist was post exposure baked (PEB) at 100° C. for 60 seconds followed by development with 0.26N aqueous tetramethylammonium hydroxide (TMAH) solution and subsequent water wash. For each example, an L/S pattern having a line width of 90 nm and a pitch of 180 nm was formed. Mask Error Factor (MEF) and Exposure Latitude (EL) were determined by top-down scanning electron microscopy (SEM) using images captured with a Hitachi 9380 CD-SEM, operating at an accelerating voltage of 800 volts (V), a probe current of 8.0 picoamperes (pA), and 200 K× magnification. Exposure latitude (EL) was defined as a difference in exposure energy to print +/−10% of the target diameter normalized by the sizing energy. Mask Error Factor (MEF) was defined as the ratio of critical dimension (CD) change for the resolved photoresist pattern to the relative dimension change on the mask pattern.

Results from lithographic evaluation of formulations from Comparative Example 1 and Example 1 are shown in Table 2.

TABLE 2

| Example | Esize (mJ/cm$^2$) | MEF | EL @ 10% of CD Target |
|---|---|---|---|
| CEx. 1 | 23.37 | 3.51 | 10.29 |
| Ex. 1 | 41.62 | 3.02 | 13.66 |

As seen in Table 2, a photoresist formulation (Ex. 1) prepared using the exemplary sulfonate PAG TPS SAdOH-TFBS above shows a higher exposure latitude (13.66) and a lower MEF (3.02) when compared with the nearly identical comparative photoresist formulation (CEx. 1;l EL 10.29, MEF 3.51) but prepared using the commercially available PAG triphenylsulfonium perfluorobutane sulfonate. Thus, Example 1 which includes the PAG TPS SAdOH-TFBS shows the improved lithographic performance based on exposure latitude (EL) and mask error factor (MEF).

All ranges disclosed herein are inclusive of the endpoints, and the endpoints are independently combinable with each other. The suffix "(s)" as used herein is intended to include both the singular and the plural of the term that it modifies, thereby including at least one of that term. "Optional" or "optionally" means that the subsequently described event or circumstance can or cannot occur, and that the description includes instances where the event occurs and instances where it does not. As used herein, "combination" is inclusive of blends, mixtures, alloys, or reaction products. All references are incorporated herein by reference.

The use of the terms "a" and "an" and "the" and similar referents in the context of describing the invention (especially in the context of the following claims) are to be construed to cover both the singular and the plural, unless otherwise indicated herein or clearly contradicted by context. Further, it should further be noted that the terms "first," "second," and the like herein do not denote any order, quantity, or importance, but rather are used to distinguish one element from another.

The invention claimed is:

1. A compound having the formula (I):

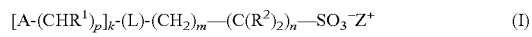

wherein

A is a substituted or unsubstituted, polycyclic, or fused polycyclic C$_5$ or greater cycloaliphatic group optionally comprising O, S, N, F, or a combination comprising at least one of the foregoing, R$^1$ is H, a single bond, or a substituted or unsubstituted C$_{1-30}$ alkyl group, wherein when R$^1$ is a single bond, R$^1$ is covalently bonded to a carbon atom of A, each R$^2$ is independently H, F, or C$_{1-4}$ fluoroalkyl, wherein at least one R$^2$ is not hydrogen, L is a linking group comprising a sulfonate group, a sulfonamide group, or a C$_{1-30}$ sulfonate or sulfonamide-containing group, Z$^+$ is an organic or inorganic cation, and p is an integer of 0 to 10, k is 1 or 2, m is an integer of 2-10, and n is an integer of 1 to 10.

2. The compound of claim 1, having the formula (IIa) or (IIb):

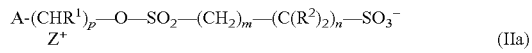

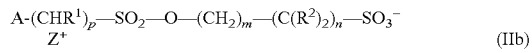

wherein A, R$^1$, R$^2$ p, m, n, and Z$^+$ are as defined for formula (I).

3. The compound of claim 1, having the formula (IIIa) or (IIIb):

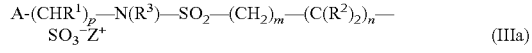

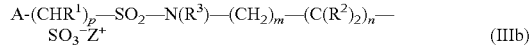

wherein A, R$^1$, R$^2$ p, m, n, and Z$^+$ are as defined for formula (I) and R$^3$ is H, a C$_{1-20}$ alkyl group, or A-(CHR$^1$)$_p$—.

4. The compound of claim 1, having the formula (IV), (V), (VI), (VII), (VIII), (IX), (X), (XI), or (XII):

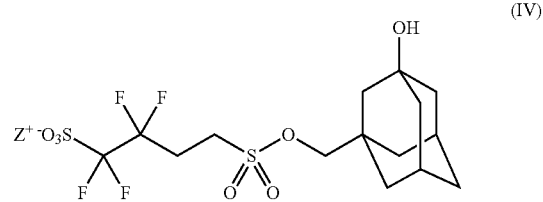

(V)
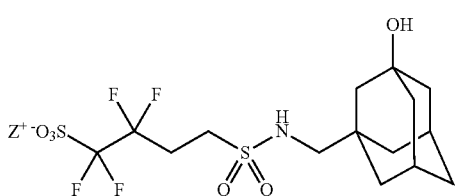

(VI)
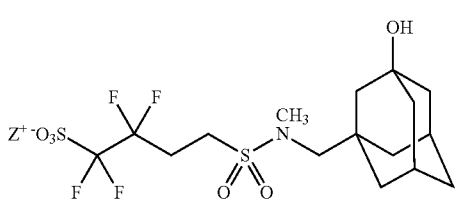

(VII)
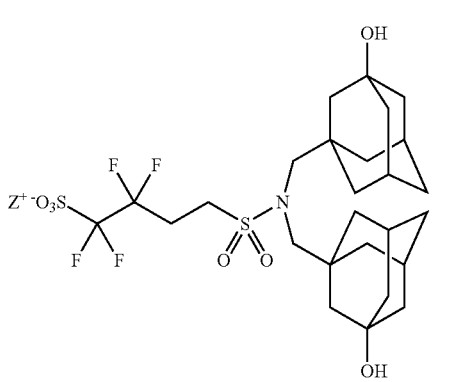

(VIII)
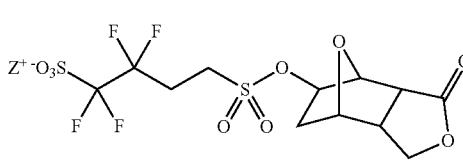

(IX)
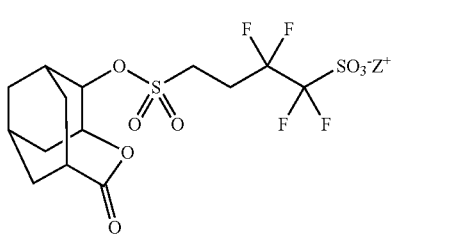

(X)
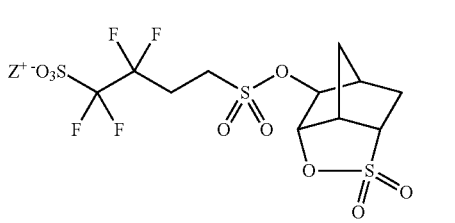

(XI)
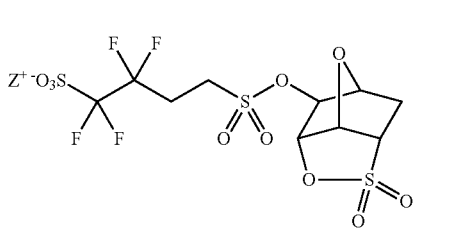

(XII)
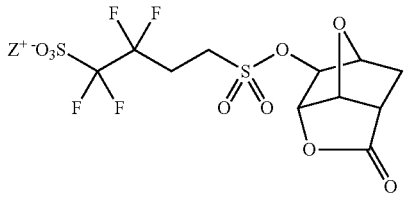

wherein $Z^+$ is as defined in formula (I).

5. The compound of claim 1, wherein $Z^+$ is a cation of the formula (XIII):

(XIII)
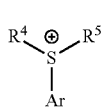

wherein $R^4$ and $R^5$ are independently substituted or unsubstituted $C_{1-20}$ alkyl, $C_{1-20}$ fluoroalkyl, $C_{3-20}$ cycloalkyl, $C_{3-20}$ fluorocycloalkyl, $C_{2-20}$ alkenyl, $C_{2-20}$ fluoroalkenyl, $C_{6-20}$ aryl, $C_{6-20}$ fluoroaryl, $C_{5-20}$ heteroaryl, $C_{7-20}$ aralkyl, $C_{7-20}$ fluoroaralkyl, $C_{6-20}$ heteroaralkyl, where $R^4$ and $R^5$ are separate or connected by a single bond, and Ar is a $C_{5-30}$ aromatic-containing group.

6. The compound of claim 5, wherein the cation is of the formula (XIV), (XV), or (XVI):

(XIV)
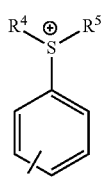

(XV)
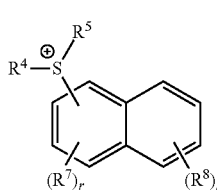

(XVI)
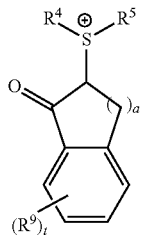

wherein
$R^4$ and $R^5$ are independently substituted or unsubstituted $C_{1-20}$ alkyl, $_{1-20}$ fluoroalkyl, $C_{3-20}$ cycloalkyl, $C_{3-20}$ fluorocycloalkyl, $C_{2-20}$ alkenyl, $C_{2-20}$ fluoroalkenyl, $C_{6-20}$ aryl, $C_{6-20}$ fluoroaryl, $C_{5-20}$ heteroaryl, $C_{7-20}$ aralkyl, $C_{7-20}$ fluoroaralkyl, or $C_{6-20}$ heteroaralkyl, where $R^4$ and $R^5$ are separate or connected by a single bond;
$R^6$, $R^7$, $R^8$ and $R^9$ are each independently H, a halogen, $C_{1-20}$ alkyl, $C_{1-20}$ fluoroalkyl, $C_{1-20}$ alkoxy, $C_{1-20}$ fluoroalkoxy, $C_{1-20}$ thioalkoxy, $C_{1-20}$ fluorothioalkoxy, $C_{1-20}$ alkoxycarbonyl, $C_{1-20}$ fluoroalkoxycarbonyl, $C_{1-20}$ thioalkoxycarbonyl, $C_{1-20}$ fluorothioalkoxycarbonyl, $C_{3-20}$ cycloalkyl, $C_{3-20}$ fluorocycloalkyl, $C_{3-20}$ cycloalkoxy, $C_{3-20}$ fluorocycloalkoxy, $C_{2-20}$ alkenyl, $C_{2-20}$ fluoroalkenyl, $C_{6-20}$ aryl, $C_{6-20}$ fluoroaryl, $C_{6-20}$ aryloxy, $C_{6-20}$ fluoroaryloxy, $C_{5-20}$ heteroaryl, $C_{5-20}$ heteroaryloxy, $C_{5-20}$ heteroaryloxy, $C_{7-20}$ aralkyl, $C_{7-20}$ fluoroaralkyl, $C_{7-20}$ aralkyloxy $C_{7-20}$ fluoroaralkyloxy, or $C_{6-20}$ heteroaralkyl, or $C_{6-20}$ heteroaralkyloxy, wherein $R^6$, $R^7$, $R^8$ and $R^9$ are each independently unsubstituted or further substituted to include an acid-labile group, a base-labile group, or a base-soluble group, and q is an integer of 1 to 5, r is an integer of 0 to 3, s is an integer of 0 to 4, t is an integer of 0 to 4, and a is an integer of 0 to 4.

7. The compound of claim 6, wherein $Z^+$ is of the formula (XVII), (XVIII), (XIX), or (XX):

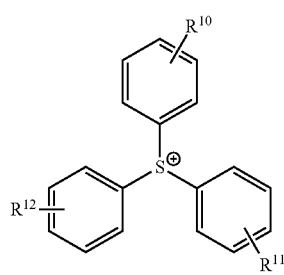
(XVII)

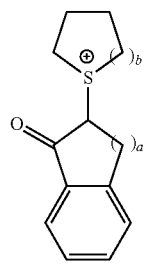
(XVIII)

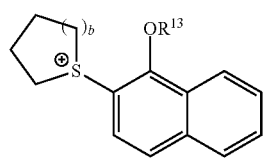
(XIX)

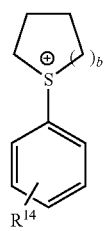
(XX)

wherein
$R^{10}$, $R^{11}$, $R^{12}$ and $R^{14}$ are independently H, a halogen, $C_{1-10}$ alkyl, $C_{1-10}$ fluoroalkyl, $C_{1-10}$ alkoxy, $C_{1-10}$ fluoroalkoxy, $C_{3-10}$ cycloalkyl, $C_{3-10}$ fluorocycloalkyl, $C_{3-10}$ cycloalkoxy, or $C_{3-10}$ fluorocycloalkoxy,
$R^{13}$ is H, $C_{1-10}$ alkyl, $C_{1-10}$ fluoroalkyl, $C_{3-10}$ cycloalkyl, or $C_{3-10}$ fluorocycloalkyl, and
a and b are each independently 1 or 2.

8. A photoresist composition, comprising:
an acid-sensitive polymer, and
a compound of claim 1.

9. A coated substrate, comprising: (a) a substrate having one or more layers to be patterned on a surface thereof; and (b) a layer of a photoresist composition of claim 8 over the one or more layers to be patterned.

10. The coated substrate of claim 9, wherein the compound of claim 1 has the formula (IIa) or (IIb):

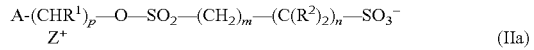
(IIa)

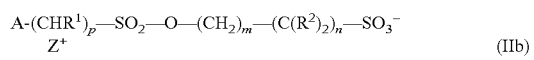
(IIb)

wherein A, $R^1$, $R^2$ p, m, n, and $Z^+$ are as defined for formula (I).

11. The coated substrate of claim 9, wherein the compound of claim 1 has the formula (IIIa) or (IIIb):

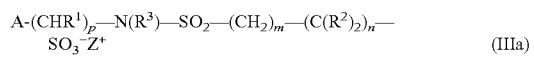
(IIIa)

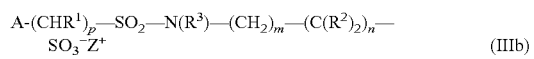
(IIIb)

wherein A, $R^1$, $R^2$ p, m, n, and $Z^+$ are as defined for formula (I), and $R^3$ is H, a $C_{1-20}$ alkyl group, or A-(CHR$^1$)$_p$—.

12. The coated substrate of claim 9, wherein the compound of claim 1 has the formula (IV), (V), (VI), (VII), (VIII), (IX), (X), (XI), or (XII):

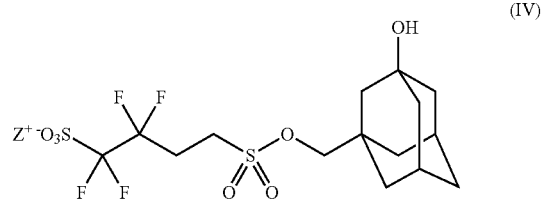
(IV)

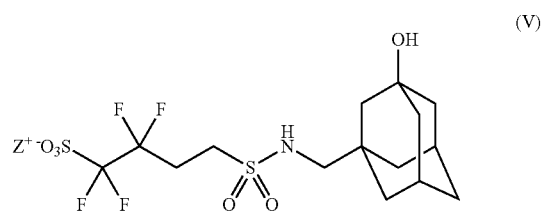
(V)

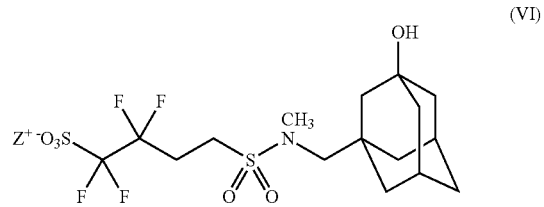
(VI)

(VII)

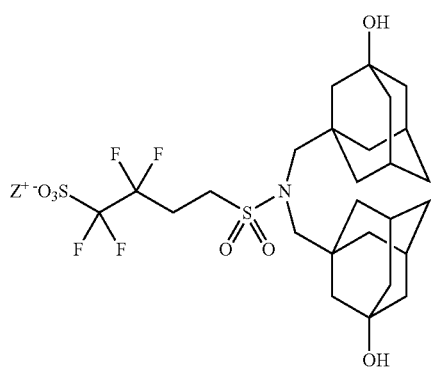

(XIII)

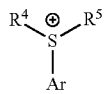

wherein $R^4$ and $R^5$ are independently substituted or unsubstituted $C_{1-20}$ alkyl, $C_{1-20}$ fluoroalkyl, $C_{3-20}$ cycloalkyl, $C_{3-20}$ fluorocycloalkyl, $C_{2-20}$ alkenyl, $C_{2-20}$ fluoroalkenyl, $C_{6-20}$ aryl, $C_{6-20}$ fluoroaryl, $C_{5-20}$ heteroaryl, $C_{7-20}$ aralkyl, $C_{7-20}$ fluoroaralkyl, $C_{6-20}$ heteroaralkyl, where $R^4$ and $R^5$ are separate or connected by a single bond, and Ar is a $C_{5-30}$ aromatic-containing group.

14. The coated substrate of claim 13, wherein the cation is of the formula (XIV), (XV), or (XVI):

(VIII)

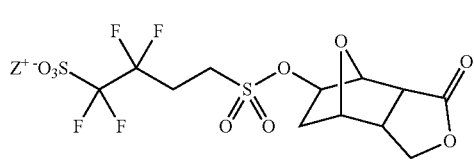

(XIV)

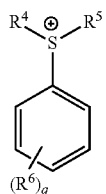

(IX)

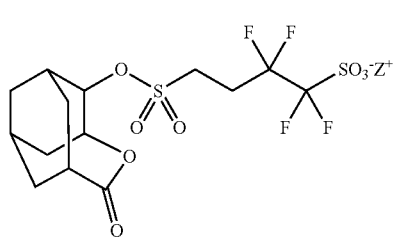

(XV)

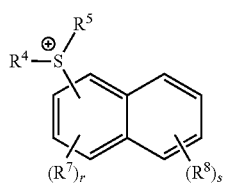

(X)

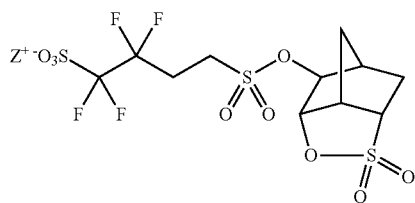

(XVI)

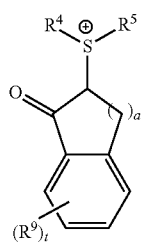

(XI)

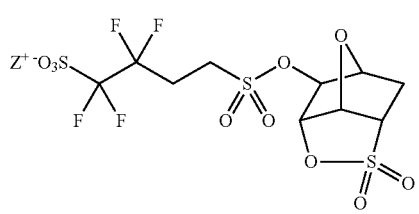

wherein
$R^4$ and $R^5$ are independently substituted or unsubstituted $C_{1-20}$ alkyl, $C_{1-20}$ fluoroalkyl, $C_{3-20}$ cycloalkyl, $C_{3-20}$ fluorocycloalkyl, $C_{2-20}$ alkenyl, $C_{2-20}$ fluoroalkenyl, $C_{6-20}$ aryl, $C_{6-20}$ fluoroaryl, $C_{5-20}$ heteroaryl, $C_{7-20}$ aralkyl, $C_{7-20}$ fluoroaralkyl, or $C_{6-20}$ heteroaralkyl, where $R^4$ and $R^5$ are separate or connected by a single bond;

$R^6$, $R^7$, $R^8$ and $R^9$ are each independently H, a halogen, $C_{1-20}$ alkyl, $C_{1-20}$ fluoroalkyl, $C_{1-20}$ alkoxy, $C_{1-20}$ fluoroalkoxy, $C_{1-20}$ thioalkoxy, $C_{1-20}$ fluorothioalkoxy, $C_{1-20}$ alkoxycarbonyl, $C_{1-20}$ fluoroalkoxycarbonyl, $C_{1-20}$ thioalkoxycarbonyl, $C_{1-20}$ fluorothioalkoxycarbonyl, $C_{3-20}$ cycloalkyl, $C_{3-20}$ fluorocycloalkyl, $C_{3-20}$ cycloalkoxy, $C_{3-20}$ fluorocycloalkoxy, $C_{2-20}$ alkenyl, $C_{2-20}$ fluoroalkenyl, $C_{6-20}$ aryl, $C_{6-20}$ fluoroaryl, $C_{6-20}$ aryloxy, $C_{6-20}$ fluoroaryloxy, $C_{5-20}$ heteroaryl, $C_{5-20}$ heteroaryloxy, $C_{5-20}$ heteroaryloxy, $C_{7-20}$ aralkyl, $C_{7-20}$ fluoroaralkyl, $C_{7-20}$ aralkyloxy $C_{7-20}$ fluoroaralkyloxy, or $C_{6-20}$ heteroaralkyl, or $C_{6-20}$ heteroaralkyloxy, wherein $R^6$, $R^7$, $R^8$ and $R^9$ are each independently unsubstituted or further substituted to include an acid-labile group, a base-labile group, or a base-soluble group, and (XII)

wherein $Z^+$ is as defined in formula (I).

13. The coated substrate of claim 9, wherein, in the compound of claim 1, $Z^+$ is a cation of the formula (XIII):

q is an integer of 1 to 5, r is an integer of 0 to 3, s is an integer of 0 to 4, t is an integer of 0 to 4, and a is an integer of 0 to 4.

15. The photoresist of claim 8, wherein the compound of claim 1 has the formula (IIa) or (IIb):

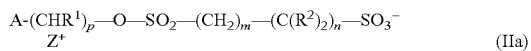
(IIa)

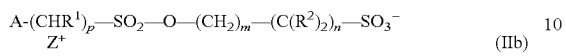
(IIb)

wherein A, R$^1$, R$^2$ p, m, n, and Z$^+$ are as defined for formula (I).

16. The photoresist of claim 8, wherein the compound of claim 1 has the formula (IIIa) or (IIIb):

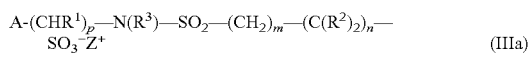
(IIIa)

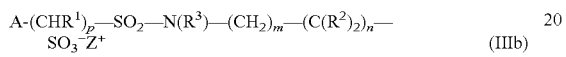
(IIIb)

wherein A, R$^1$, R$^2$ p, m, n, and Z$^+$ are as defined for formula (I), and R$^3$ is H, a C$_{1-20}$ alkyl group, or A-(CHR$^1$)$_p$—.

17. The photoresist of claim 8, wherein the compound of claim 1 has the formula (IV), (V), (VI), (VII), (VIII), (IX), (X), (XI), or (XII):

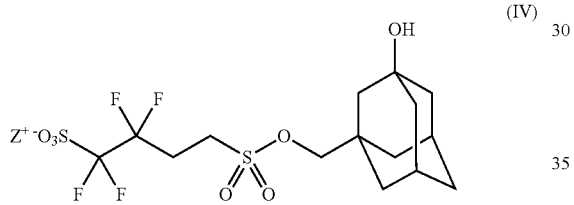
(IV)

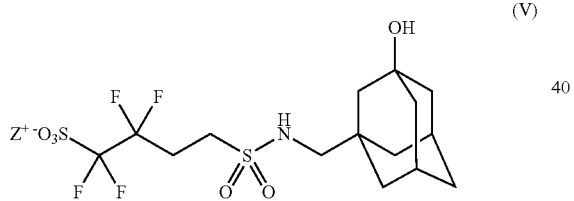
(V)

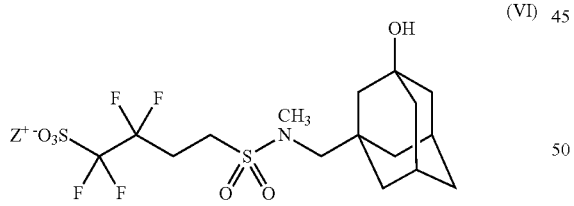
(VI)

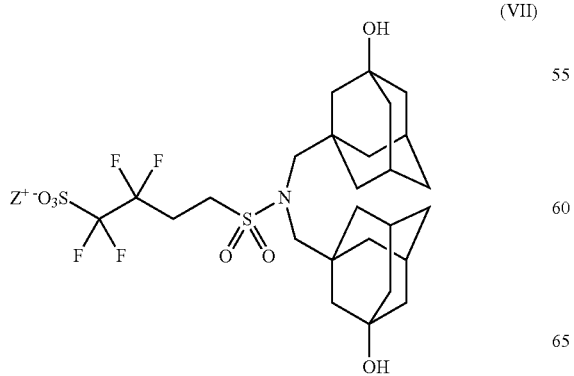
(VII)

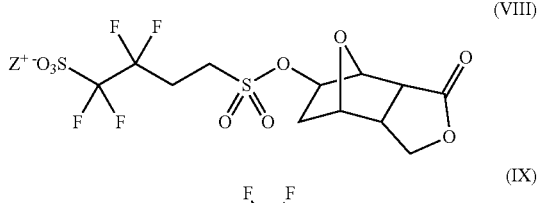
(VIII)

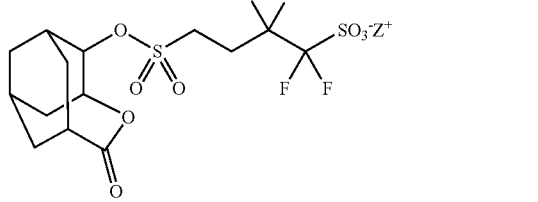
(IX)

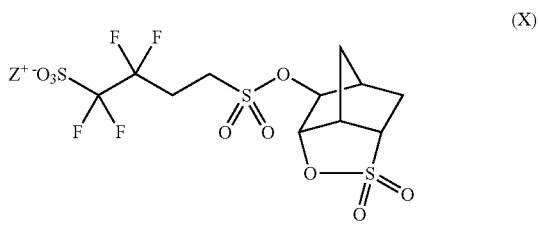
(X)

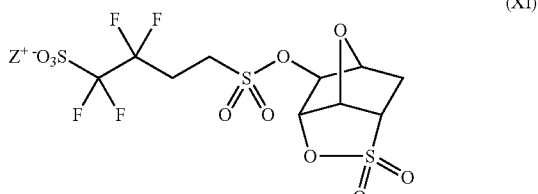
(XI)

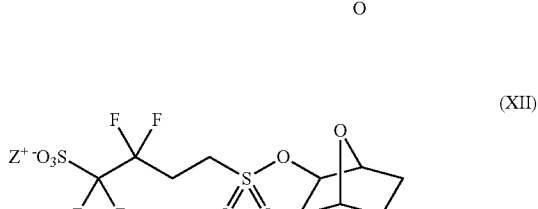
(XII)

wherein Z$^+$ is as defined in formula (I).

18. The photoresist of claim 8, wherein, in the compound of claim 1, Z$^+$ is a cation of the formula (XIII):

(XIII)

wherein R$^4$ and R$^5$ are independently substituted or unsubstituted C$_{1-20}$ alkyl, C$_{1-20}$ fluoroalkyl, C$_{3-20}$ cycloalkyl, C$_{3-20}$ fluorocycloalkyl, C$_{2-20}$ alkenyl, C$_{2-20}$ fluoroalkenyl, C$_{6-20}$ aryl, C$_{6-20}$ fluoroaryl, C$_{5-20}$ heteroaryl, C$_{7-20}$ aralkyl, C$_{7-20}$ fluoroaralkyl, C$_{6-20}$ heteroaralkyl, where R$^4$ and R$^5$ are separate or connected by a single bond, and Ar is a C$_{5-30}$ aromatic-containing group.

19. The photoresist of claim 18, wherein the cation is of the formula (XIV), (XV), or (XVI):

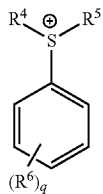
(XIV)

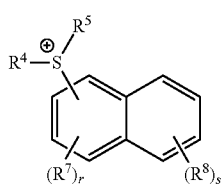
(XV)

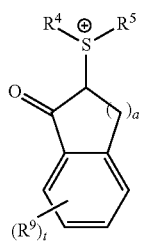
(XVI)

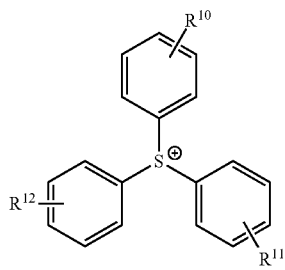
(XVII)

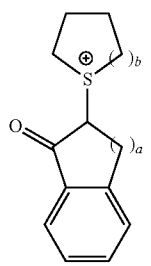
(XVIII)

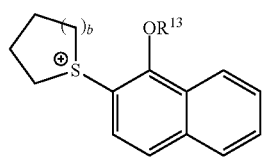
(XIX)

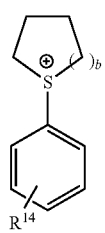
(XX)

wherein $R^4$ and $R^5$ are independently substituted or unsubstituted $C_{1-20}$ alkyl, $C_{1-20}$ fluoroalkyl, $C_{3-20}$ cycloalkyl, $C_{3-20}$ fluorocycloalkyl, $C_{2-20}$ alkenyl, $C_{2-20}$ fluoroalkenyl, $C_{6-20}$ aryl, $C_{6-20}$ fluoroaryl, $C_{5-20}$ heteroaryl, $C_{7-20}$ aralkyl, $C_{7-20}$ fluoroaralkyl, or $C_{6-20}$ heteroaralkyl, where $R^4$ and $R^5$ are separate or connected by a single bond;

$R^6$, $R^7$, $R^8$ and $R^9$ are each independently H, a halogen, $C_{1-20}$ alkyl, $C_{1-20}$ fluoroalkyl, $C_{1-20}$ alkoxy, $C_{1-20}$ fluoroalkoxy, $C_{1-20}$ thioalkoxy, $C_{1-20}$ fluorothioalkoxy, $C_{1-20}$ alkoxycarbonyl, $C_{1-20}$ fluoroalkoxycarbonyl, $C_{1-20}$ thioalkoxycarbonyl, $C_{1-20}$ fluorothioalkoxycarbonyl, $C_{3-20}$ cycloalkyl, $C_{3-20}$ fluorocycloalkyl, $C_{3-20}$ cycloalkoxy, $C_{3-20}$ fluorocycloalkoxy, $C_{2-20}$ alkenyl, $C_{2-20}$ fluoroalkenyl, $C_{6-20}$ aryl, $C_{6-20}$ fluoroaryl, $C_{6-20}$ aryloxy, $C_{6-20}$ fluoroaryloxy, $C_{5-20}$ heteroaryl, $C_{5-20}$ heteroaryloxy, $C_{5-20}$ heteroaryloxy, $C_{7-20}$ aralkyl, $C_{7-20}$ fluoroaralkyl, $C_{7-20}$ aralkyloxy $C_{7-20}$ fluoroaralkyloxy, or $C_{6-20}$ heteroaralkyl, or $C_{6-20}$ heteroaralkyloxy, wherein $R^6$, $R^7$, $R^8$ and $R^9$ are each independently unsubstituted or further substituted to include an acid-labile group, a base-labile group, or a base-soluble group, and q is an integer of 1 to 5, r is an integer of 0 to 3, s is an integer of 0 to 4, t is an integer of 0 to 4, and a is an integer of 0 to 4.

20. The photoresist of claim 19, wherein $Z^+$ is of the formula (XVII), (XVIII), (XIX), or (XX):

wherein $R^{10}$, $R^{11}$, $R^{12}$ and $R^{14}$ are independently H, a halogen, $C_{1-10}$ alkyl, $C_{1-10}$ fluoroalkyl, $C_{1-10}$ alkoxy, $C_{1-10}$ fluoroalkoxy, $C_{3-10}$ cycloalkyl, $C_{3-10}$ fluorocycloalkyl, $C_{3-10}$ cycloalkoxy, or $C_{3-10}$ fluorocycloalkoxy, $R^{13}$ is H, $C_{1-10}$ alkyl, $C_{1-10}$ fluoroalkyl, $C_{3-10}$ cycloalkyl, or $C_{3-10}$ fluorocycloalkyl, and a and b are each independently 1 or 2.

21. A compound having the formula (IV), (V), (VI), (VII), (VIII), (IX), (X), (XI), or (XII):

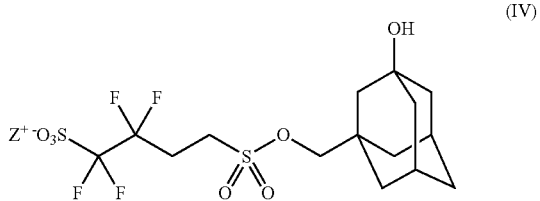
(IV)

(V)
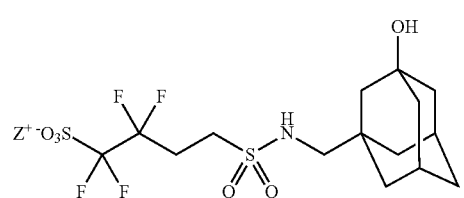
(VI)
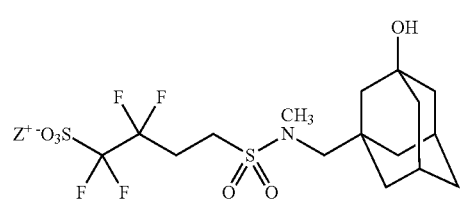
(VII)
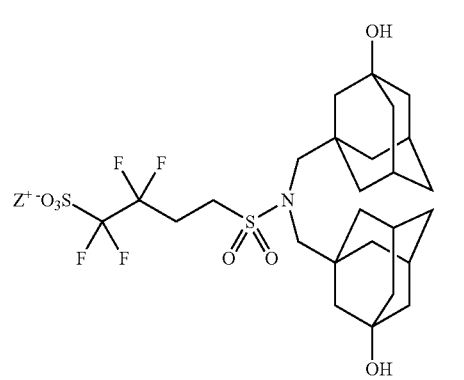
(VIII)
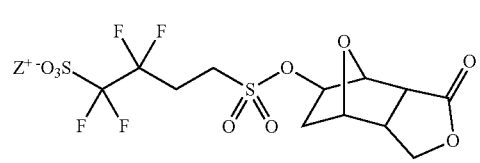
(IX)
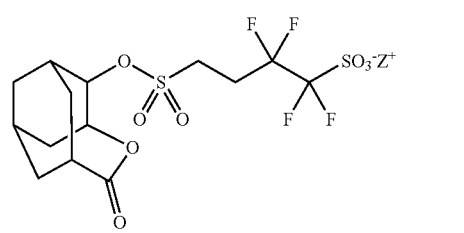
(X)
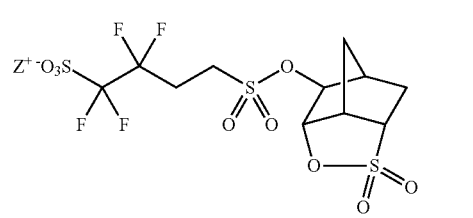
(XI)
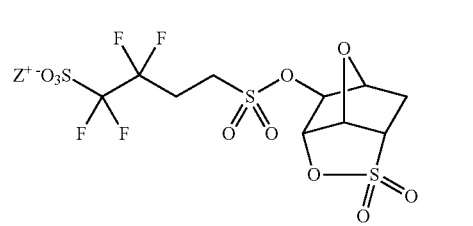
(XII)
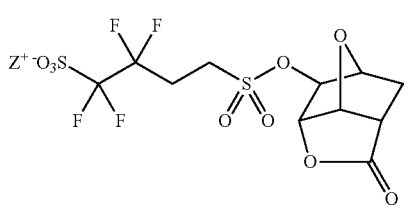
wherein Z' is as defined in formula (I).
22. A photoresist composition comprising:
an acid-sensitive polymer, and
a compound having the formula (IV), (V), (VI), (VII), (VIII), (IX), (X), (XI), or (XII):
(IV)
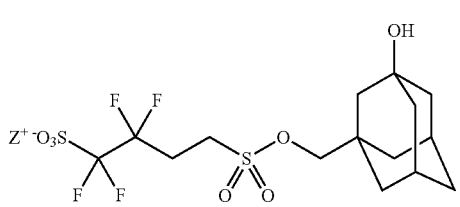
(V)
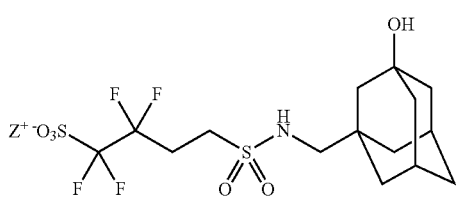
(VI)
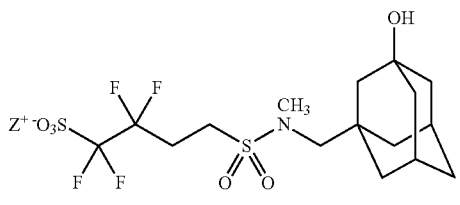
(VII)
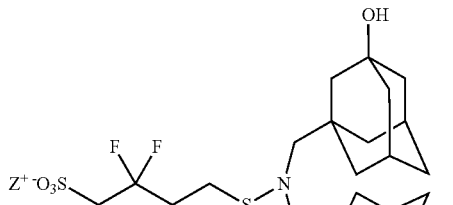
(VIII)
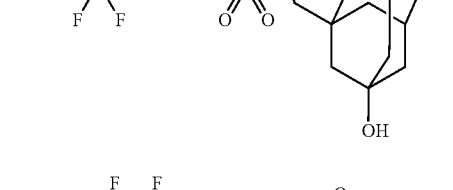

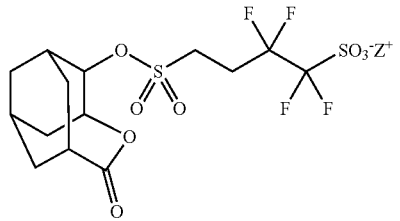
(IX)
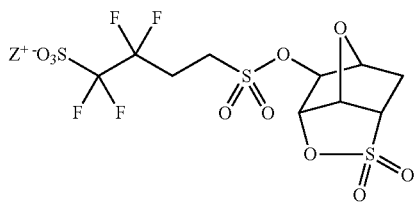
(XI)
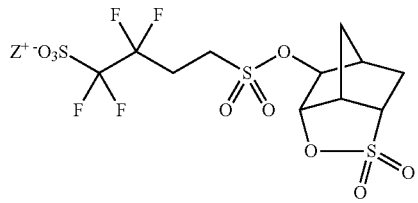
(X)
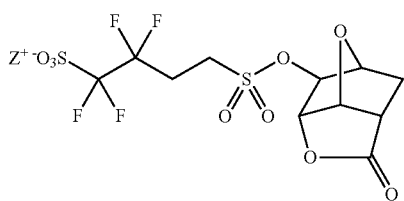
(XII)
wherein Z' is as defined in formula (I).
* * * * *